United States Patent

Plotkin et al.

Patent Number: 5,159,098
Date of Patent: Oct. 27, 1992

[54] ALK-1-ENYLOXY CARBAMATES

[75] Inventors: Jeffrey S. Plotkin, Monsey, N.Y.; Kolazi S. Narayanan, Palisades Park, N.J.

[73] Assignee: ISP Investments Inc., Wilmington, Del.

[21] Appl. No.: 579,511

[22] Filed: Sep. 10, 1990

[51] Int. Cl.$^5$ .............................................. C07C 68/02
[52] U.S. Cl. .................. 558/275; 558/267; 558/268; 558/276
[58] Field of Search ............ 558/275, 276; 560/166, 560/160, 161, 164, 158, 26, 29, 30, 33

[56] References Cited

U.S. PATENT DOCUMENTS

| | | | |
|---|---|---|---|
| 2,921,955 | 1/1960 | Newman | 558/276 |
| 4,199,526 | 4/1980 | Senet et al. | 558/276 |
| 4,463,141 | 7/1984 | Robinson | 558/276 |

*Primary Examiner*—Arthur C. Prescott
*Attorney, Agent, or Firm*—Marilyn J. Maue; Joshua J. Ward

[57] ABSTRACT

The invention relates to alk-1-enyloxy carbamates selected from the group having the formulae

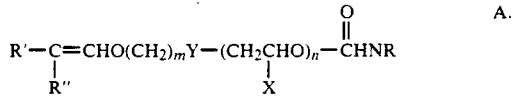

and

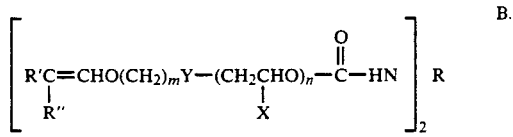

wherein R is a saturated or unsaturated, monovalent or divalent hydrocarbon radical having from 1 to 50 carbon atoms and is optionally substituted with halo, alkyleneoxy, hydroxy, or a combination of said radicals; Y is —O— or —OCO—O—; X is hydrogen or methyl; R' and R" are each independently hydrogen, alkyl, aryl, aralkyl or alkaryl; m has a value of from 2 to 6 and n has a value of from 0 to 25. The invention also relates to the use of these alk-1-enyloxy carbamates as reactive diluents in cationically induced radiation curing of epoxy, vinyl ether, urethane monomers or oligomers and others.

12 Claims, No Drawings

ALK-1-ENYLOXY CARBAMATES

In one aspect the invention relates to alk-1-enyloxy carbamates which are rapidly curable by cationic radiation. In another aspect the invention relates to the use of said products as protective coatings, reactive diluents for other polymerizable compounds or as photoresist materials.

BACKGROUND OF THE INVENTION

Certain radiation curable coatings and films such as those formed from the acrylates, particularly trimethylol propane triacrylate, trimethacrylate, pentaerythritol triacrylate, and hexanediol diacylate or methacrylate, are in great demand because of their rapid curing properties. However, these compounds are normally highly viscous liquids or solids and thus are unsuitable as diluents for other polymeric components of a radiation curable formulation. Indeed, such compounds themselves require the incorporation of a diluent or solvent for uniform substrate coating, control of coating thickness and curing at low temperatures. Accordingly, low viscosity monofunctional diluents are usually included in their formulations. While these diluents are reactive, they materially reduce the cross-linked density of the finished product and consequently lower abrasion resistance and ability to withstand chemical attack.

Although solvents have been used to reduce viscosity, they are detrimental in radiation curing due to their volatility which presents problems for uniform composition control unless their evaporation prior to radiant exposure is effected. Obviously, such procedure extends processing time and may pose environmental drawbacks.

To some extent, the drawbacks of high viscosity monomers can be reduced by curing at elevated temperatures. However, this alternative significantly adds to the cost of the overall operation in the expenditure of energy, temperature control and loss of more volatile components in the composition or blistering of the coating resulting from entrained volatiles.

Since acrylate monomers are not conducive to cationically induced radiation curing, they require more costly free radical systems which are oxygen inhibited unless effected in an inert atmosphere, generally under a blanket of nitrogen. Although formulation with a photoinitiator which undergoes bimolecular reaction with a hydrogen donor minimizes the inhibitory effect of air, this benefit is realized at the expense of a greatly reduced cure rate. Also, it is found that polymerization or curing in free radical systems ceases almost immediately upon removal from the source of radiation; thus, the cured product usually contains significant amounts of unpolymerized components. Accordingly, it is an aim of research to develop a monomer having the beneficial properties of acrylates but which is amenable to radiation curing at a rapid rate by cationically induced polymerization which is not oxygen inhibited and which permits continued polymerization after removal from the source of radiation exposure.

Finally, it is noted that the unsubstituted acrylates are sensitizers and skin irritants as well as being carcinogenic, so that specialized safety precautions must be taken to protect operators from exposure. Although alkoxylation has lessened irritancy of the acrylates, their carcinogenic properties are not reduced.

The inherent deficiencies of the acrylate systems can be partially overcome by the use of epoxy resins. Epoxy resins can be polymerized by normal radiation techniques using cationic photoinitiators such as iodonium, sulfonium and ferrocene salts, hexafluorophosphate, hexafluoroantimonate and hexafluoroarsonate to produce a tack free film. Although in such formulations tack free products are almost immediately obtained, polymerization of the mixture is incomplete. It is well known that the polymerization of epoxy resins is extremely slow and requires as much as several days to achieve their ultimate physical properties. Thus, thermal curing is often employed to increase the rate of polymerization.

Certain allyl compounds also have been used as coatings; however these monomers and their oligomers are not readily curable by cationic radiation. Thermal curing is generally required to increase the rate of polymerization. While allyl ethers such as polyethylene glycols are curable by UV light, they require a free radical initiated reaction which proceeds at a slow rate, generally over a period of from 2 to 10 hours in order to reach completion.

Accordingly it is an object of the present invention to overcome the above described deficiencies by employing an economical and commercially acceptable compound or composition and curing process.

Another object of this invention is to utilize a multifunctional cross-linking agent, which is itself a polymerizable viscous liquid and which assists rapid radiation curing of allyl or epoxide monomers and oligomers.

Another object is to provide a non-toxic cross linkable compound which is suitably cured as a film or as a coating on a substrate and which possesses toughness, good adhesion, abrasion resistance and resistance to chemical attack in acid or basic media.

Still another object is to provide a more economical process for cross-linking monomeric or polymeric allyl or epoxy ethers within a few seconds which can be effected in the presence of air.

Another object is to provide a compound which is curable at a rapid rate by cationically induced radiation.

These and other objects will become apparent from the following description and disclosure.

THE INVENTION

In accordance with this invention there is provided an alk-1-enyloxy carbamate selected from the group having the formulae

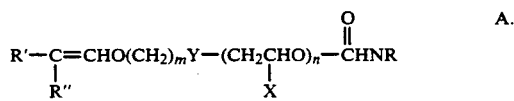

A.

and

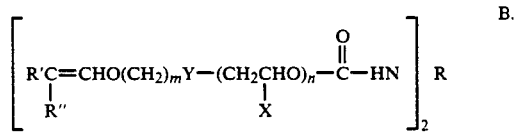

B.

wherein R is a saturated or unsaturated, monovalent or divalent hydrocarbon radical having from 1 to 50 carbon atoms of the group alkyl, alkenyl, alkynyl, aryl, alkaryl, aralkyl and aralkenyl radicals which radicals are optionally substituted with halo, alkyleneoxy, hydroxy, or a combination of said radicals; Y is —O— or —OCO—O—; X is hydrogen or methyl; R' and R" are each independently hydrogen, alkyl, aryl, aralkyl or alkaryl; m has a value of from 2 to 6 and n has a value of from 0 to 25.

Of the above, the preferred compounds are those wherein at least one of R' and R" is hydrogen and R is an aliphatic hydrocarbon radical having from 2 to 20 carbon atoms or

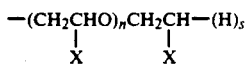

wherein s has a value of one in compound A and s has a value of zero in compound B.

The present compounds are readily prepared by reacting an amino compound having the formula

with a dialk-1-enyl ether carbonate having the formula

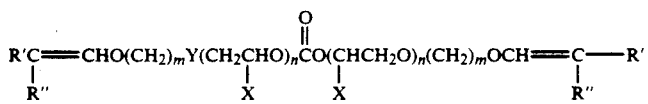

wherein R, R', R", Y, X, m and n are as defined and wherein (a) has a value of zero or one, i.e. (a) is zero when product A is produced and (a) is one when product B is produced.

The reactions of this invention are defined by the equations

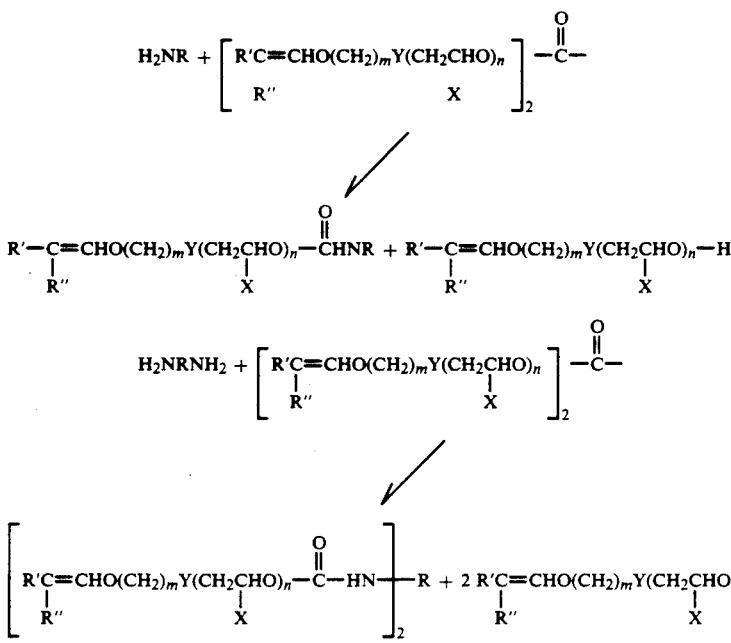

The above reactions are conducted in the presence of between about 0.01 and about 5 wt. %, preferably between about 0.1 and about 1 wt. % of a basic catalyst such as sodium, potassium or lithium hydroxide, hydride or alkylate, e.g. methylate, and the like. The reactants may be diluted with up to 80% of a suitable inert solvent such as xylene, toluene, tetrahydrofuran, N-methylpyrrolidone, dimethylformamine, etc. Although dilution is usually recommended for more viscous reaction mixtures, it is also within the scope of this invention to carry out the reaction in the absence of solvent.

The reaction conditions include a temperature of from about 50° to about 200° C., a pressure of from about 1 mm Hg to about 100 atmospheres for a period of from about 0.5 to about 24 hours. Within the above operating parameters, between about 90° and about 120° C. under from about 1 to about 10 mm Hg for a period of from about 3 to about 10 hours are preferred. High conversions in excess of 80% are achieved by the present reaction.

Examples of suitable amino reactants include ethylamine, propylamine, butylamine, tetracontamine, octylamine, isooctylamine, dodecylamine, cyclohexylamine, 1,6-diaminohexane, 1,6-diaminocyclohexane, 1,5-diaminodecane, 1,16-diaminohexadecane, 1,4-diaminobutane, 1,2-diaminoethane, α,ω-diaminoeicosane, α,ω-diaminopentacosane, etc. and ethoxylated or propoxylated derivatives thereof.

Suitable dialk-1-enyloxy carbonate reactants include the oxy di(4-butenyl) carbonate of diethylene glycol, the bis-(4-vinyloxy butyl carbonate) of cyclohexanediol, the bis[4-(vinyloxy)butyl carbonate]of 2-butene-1,4-diol, bis[4-(vinyloxy)butyl carbonate]; di(-pent-1-enyloxy) methyl carbonate; divinyloxy butyl carbonate of triethylene glycol; 2-methyl-pent-1-enyloxy propyl carbonate of tetrapropylene glycol, methyl(4-vinyloxy butyl carbonate); phenyl vinyloxy butyl carbonate; benzyl vinyloxy ethyl carbonate; the divinyloxybutyl carbonate of diethylene glycol and the like.

The ratio of amine reactant to dialk-1-enyloxy carbonate is as close to stoichiometry of the product desired, as is convenient to maintain. Desirably, the amount of dialk-1-enyloxy carbonate varies from about 1 to about 2 moles of carbonate per mole of amino compound. However, it is to be understood that excess amounts of the alk-1-enyloxy carbonate, up to about a 10 mole excess, can be employed without detriment to the reaction; the only objection being that such high excesses of the carbonate reactant are wasteful and inefficient.

The above compounds or crude product mixtures of the alk-1-enyloxy carbamate with unreacted alk-1-enyloxy carbonate or a mixture thereof with other co-polymerizable monomers or oligomers such as epoxides, vinyl ethers, urethanes etc., in amounts up to about 50%, can be applied to porous or non-porous substrates in a thickness of from about 0.1 to about 20 mils, preferably from about 0.5 to about 10 mils. Suitable substrates include wood, glass, ceramic, metal, plastic, leather, masonary and fabrics. The coated material is then subjected to a source of radiation for curing.

Curing is effected in the presence of a cationic photo-initiator such as an onium salt, for example the triphenyl sulfonium salt of phosphorous hexafluoride, diphenyl iodium salt, tetrazolium chloride, phenyl onium salts or aryl alkyl onium salts and the like. Also, mixtures of the above cationic initiator and a free radical initiator can be employed. Examples of suitable free radical initiators include 1-hydrocyclohexyl phenyl ketone (e.g. IRGA-CURE 184), 2-hydroxy-2-methyl-1-phenyl-1-propan-1-one (DAROCUR 1173), 2,2-dichloro-1-(4-phenoxyphenyl) ethanone (SANDORAY 1000) and those described by M. J. M. Abadie, Advantages and Development of Photochemical Initiators, in the European Coatings Journal 5/1988, pages 350-358. When initiator mixtures are employed, the free radical component can comprise up to 75%, preferably between about 30 and about 70%, of the initiator component. A particularly preferred initiator mixture includes between about 30 wt. % and about 40 wt. % of FX-512 and between about 60 and about 70% of IRGACURE 184. The present cationic initiator or cationic/free radical initiator mixtures provide the benefits of this invention when used for cross-linking vinyl ether or epoxide monomers with the present vinyl ether carbamates. However, when the blend contains an acrylate polymerizable co-monomer the initiator mixture is recommended. The total amount of initiator employed is generally between about 0.05 and about 5 wt. %, preferably between about 0.1 and about 2 wt. % with respect to reactants. Curing is accomplished within a few seconds, most often within a period of less than one second, by exposure to a source of radiation such as UV light exposure at 100-1500 millijoules/cm$^2$, preferably from about 200 to about 600 millijoules/cm$^2$, or electron beam at from about 0.5 to about 20 megarads, preferably from about 1 to about 10 megarads, or lazer emission at equivalent exposure. Specific techniques for radiation curing are well known and require no further amplification.

The protective films formed on the substrate are clear, hard finishes having high resistance to abrasion and chemical attack from acids and bases. Because of their sensitivity to radiation, the present compounds can also be employed as photoresist materials.

Having thus described the invention reference is now had to the accompanying examples which illustrate preferred embodiments but which are not to be construed and limiting to the scope of the invention as more broadly defined above and in the appended claims.

EXAMPLE 1

Preparation of
$H_2C=CHO(CH_2)_4OCONH(CH_2)_{11}CH_3$

Into a glass 250 ml round bottom flask was charged 51.6 g. (0.2 mole) of bis(vinyloxybutyl) carbonate, 37 g. (0.2 mole) of dodecylamine and 0.5 g. of sodium methoxide. The resulting mixture was heated to 100°-105° C. at a pressure of 10 mm Hg for 8 hours in a distillation apparatus to remove unreacted amine and hydroxy butyl vinyl ether as distillate. Gas chromatographic analysis indicated 40% completion of the reaction. The distilland in the flask was vinyloxybutyl dodecyl carbamate product containing about 65 wt. % of unreacted bis(vinyloxybutyl) carbonate, which mixture is radiation curable with a cationic initiator and has properties similar to urethane coatings.

EXAMPLE 2

Preparation of
$CH_2=CHO(CH_2)_4-OCO-NH(CH_2)_{11}CH_3$

The procedure of Example 1 was repeated with a charge of 34.8 g. (0.2 mole) of methyl vinyloxybutyl carbonate, 37 g. (0.2 mole) of dodecylamine and 0.5 g. of sodium methoxide. The resulting mixture was heated to 70°-80° C. under 20-25 mm Hg for 4 hours and then at 100°-105° C. at 10 mm Hg for an additional 4 hours to remove methanol by-product containing a trace of hydroxybutyl vinyl ether and dodecylamine as distillate. The distilland was vinyloxybutyl dodecyl carbamate in about 50 wt. % yield and can be employed directly as a soft irradiation cationically curable coating on wood or on other substrates where soft coating are desirable.

Alternatively, unreacted methyl vinyloxybutyl carbonate can be separated from the vinyloxybutyl dodecyl carbamate product and the separated product used as a reactive diluent in cationically cured coatings.

EXAMPLE 3

Preparation of
$H_2C=CHO(CH_2)_4OCO-NH(CH_2)_6NHCO-O(CH_2-)_4OCH=CH_2$

The procedure of Example 1 was repeated with a charge of 103.2 g. (0.4 mole) of bis(vinyloxybutyl) carbonate, 23.2 g. (0.2 mole) of hexamethylene diamine and 0.5 g. of sodium methoxide. The resulting mixture was heated to 100°-105° C. under 100-105 mm Hg for a period of 4 hours after which heating was continued for an additional 4 hours at a reduced pressure of 10 mm Hg to remove hydroxybutyl vinyl ether and unreacted hexamethylene diamine. The distilland remaining in the flask was a 60-40 mixture of bis(vinyloxybutyl) carbamate and unreacted bis(vinyloxybutyl) carbonate, which mixture is directly curable in a cationically initiated system after the removal of the sodium methoxide catalyst by filtration.

EXAMPLE 4

Preparation of
$[H_2C=CHO(CH_2)_4OCO-O(CH_2CH_2O)_3-CONH]_2(CH_2)_6$

The procedure of Example 1 was repeated with a charge of 80.4 g. (0.2 mole) of the bis(vinyloxybutyl carbonate) of triethylene glycol, 11.6 g. of hexamethylene diamine and 0.5 g. of sodium methoxide. The resulting mixture was heated to 100°-105° C. under 100 mm Hg for a period of 4 hours, after which heating was continued for an additional 4 hours at a reduced pressure of 10 mm Hg to remove hydroxybutyl vinyl ether and unreacted hexamethylene diamine. The distilland remaining in the flask was a 40-60 mixture of the bis(vinyloxybutyl) carbonate triethylene glycol hexamethylene carbamate and the bis(vinyloxybutyl) carbonate of triethylene glycol starting material. This product mixture is curable by cationically initiated radiation suitable as protective coatings for wood and other substrates.

What is claimed is:

1. A alk-1-enyloxy carbamate selected from the group having the formulae

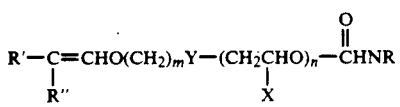

and

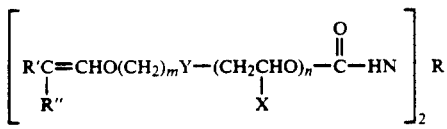

wherein R is a saturated or unsaturated, monovalent or divalent hydrocarbon radical having from 1 to 50 carbon atoms and is optionally substituted with halo, alkyleneoxy, hydroxy, or a combination of said radicals; Y is —O— or —OCO—O—; X is hydrogen or methyl; R' and R" are each independently hydrogen, alkyl, aryl, aralkyl or alkaryl; m has a value of from 2 to 6 and n has a value of from 0 to 25.

2. The alk-1-enyloxy carbamate of claim 1 having formula A wherein R is $C_1$ to $C_{20}$ alkyl, $C_2$ to $C_3$ alkoxylated alkyl, alkenyl, alkynyl, aryl, alkaryl, aralkyl or aralkenyl.

3. The alk-1-enyloxy carbamate of claim 1 having formula B wherein R is $C_2$ to $C_{20}$ alkylene, $C_2$ to $C_3$ alkoxylated alkylene, alkenylene, alkynylene, arylene, alkarylene, aralkylene or arylenealkenyl.

4. The alk-1-enyloxy carbamate of claims 1 or 3 wherein R is an aliphatic radical.

5. The alk-1-enyloxy carbamate of one of claims 1-3 wherein at least one of R' and R" is hydrogen.

6. The alk-1-enyloxy carbamate of claim 1 having formula A wherein n is zero, R is $C_8$ to $C_{20}$ alkyl and Y is —O—.

7. The alk-1-enyloxy carbamate of claim 2 wherein R is dodecyl.

8. The alk-1-enyloxy carbamate of claim 1 having formula B wherein n is a positive integer, R is $C_8$ to $C_{20}$ alkylene and Y is —O—CO—O—.

9. A composition comprising the alk-1-enyloxy carbamate of one of claims 1-8 in admixture with up to 50 wt. % of a polymerizable compound selected from the group of a vinyl ether, an epoxide, a urethane and an acrylate and a cationic polymerization initiator.

10. The process of coating the composition of claim 9 on a substrate and curing said composition in a dry state by exposure to a source of radiation.

11. The alk-1-enyloxy carbamate of claim 1 wherein R is an aliphatic radical and at least one of R' and R" is hydrogen.

12. The alk-1-enyloxy carbamate of claim 3 wherein R is an aliphatic radical and at least one of R' and R" is hydrogen.

* * * * *